United States Patent [19]

Miyata et al.

[11] 4,319,018

[45] Mar. 9, 1982

[54] PROCESS FOR PRODUCING POLYMETHYLENE POLYPHENYL POLYCARBAMATES

[75] Inventors: Katsuharu Miyata; Seiji Hasegawa; Shinobu Aoki, all of Yokohama; Isao Hara, Kanagawa, all of Japan

[73] Assignee: Mitsui Toatsu Chemicals, Inc., Tokyo, Japan

[21] Appl. No.: 164,513

[22] Filed: Jul. 2, 1980

[30] Foreign Application Priority Data

Jul. 9, 1979 [JP] Japan .................................. 54-85872

[51] Int. Cl.³ .............................................. C08G 12/26
[52] U.S. Cl. .................................... 528/232; 528/266; 560/25
[58] Field of Search .................. 528/232, 266; 560/25

[56] References Cited

U.S. PATENT DOCUMENTS

| | | | |
|---|---|---|---|
| 2,946,768 | 7/1960 | Klauke et al. | 260/65 |
| 4,146,727 | 3/1979 | Shawl et al. | 560/25 |
| 4,162,362 | 7/1979 | Shawl | 560/25 |
| 4,163,019 | 7/1979 | Mango | 260/453 P |
| 4,172,948 | 10/1979 | Shawl | 560/25 |
| 4,202,986 | 5/1980 | Shawl | 560/25 |

FOREIGN PATENT DOCUMENTS

1042891  11/1958  Fed. Rep. of Germany.

*Primary Examiner*—Lucille M. Phynes
*Attorney, Agent, or Firm*—Fisher, Christen & Sabol

[57] ABSTRACT

It is disclosed that, in the process for producing polymethylene polyphenyl polycarbamates through the reaction of N-phenyl carbamate with formaldehyde or a formaldehyde-supplying substance in the presence of an acid catalyst, if the reaction is carried out in the concurrent presence of at least one compound or a mixture of at least two compounds selected from the group consisting of N-carboalkoxy (or cycloalkoxy)-2-oxa-4-azanaphthalenes, bis(N-carboalkoxy(or cycloalkoxy)-anilino)-methanes and N,N'-dicarboalkoxy (or cycloalkoxy)aminobenzyl-anilines, the object product, polymethylene polyphenyl polycarbamate, can be obtained at a high yield. According to the present invention, also a more economical and easily aperable process for producing polymethylene polyphenyl polycarbamate is provided, by the recycling use of the named compound or compounds which have been concurrently present in the reaction system and after the reaction separated and recovered from the reaction product, and also by the recycling use of the aqueous acid solution which has been used as the catalyst, without the interceding removal of organic impurities formed in the reaction but simply with the adjustment of its acid concentration to the predetermined level.

20 Claims, No Drawings

PROCESS FOR PRODUCING POLYMETHYLENE POLYPHENYL POLYCARBAMATES

BACKGROUND OF THE INVENTION (1) Field of the Invention

This invention relates to an improvement in the process for making polymethylene polyphenyl polycarbamate, from N-phenyl carbamate and formaldehyde as the starting materials.

More particularly, the invention relates to an improved process for making polymethylene polyphenyl polycarbamate through the reaction of N-phenylcarbamate with formaldehyde in the presence of an acid catalyst, the characteristic feature residing in that the quality and yield of the object product are markedly improved by practicing the reaction in the concurrent presence of a compound or compounds having specific structures. The invention also relates to an improved production process, which is characterized in that, when the reaction is effected in the presence of an aqueous acid solution as the catalyst, the aqueous acid solution separated and recovered from the reaction system after the reaction is repetitively re-used many times under specific conditions.

(2) Description of the Prior Art

Polymethylene polyphenyl polycarbamate is a valuable substance as a starting material for agricultural chemicals and medicines, polyamide and polyurethane. Upon pyrolysis, polymethylene polyphenyl polycarbamate can also produce the corresponding polymethylene polyphenyl polyisocyanate. The development of an industrially advantageous method for its production has therefore been much awaited.

It is known to react polymethylene polyphenyl polyisocyanate with an alcohol to produce the corresponding polymethylene polyphenyl polycarbamate. This method however requires the use of strongly toxic aniline or phosgene for making the starting polymethylene polyphenyl polyisocyanate, and the method itself is very complex.

Also a process for reacting polymethylene polyphenyl polyamine with an alkyl ester or chloroformic acid to make the corresponding polymethylene polyphenyl polycarbamate has been known. Both of the starting materials, i.e., polymethylene polyphenyl polyamine and alkyl chloroformate exhibit strong toxicity or irritating property and are difficult of handling. The process also is complicated, and cannot be said an industrial process.

As a still another process for making polymethylene polyphenyl polycarbamate, that reacting N-phenyl carbamate with formaldehyde is known. For example, West German Pat. No. 1,042,891 and U.S. Pat. No. 2,946,768 disclose the formation of a condensation product by heating N-phenyl carbamate and formaldehyde together with an aqueous hydrochloric acid. The literatures however are entirely silent on the structure and composition of the product. In our reproduction of the last process, the reaction progressed very slowly, and the product contained large amounts of unreacted N-phenyl carbamate and by-products. Naturally the yield and the selectivity for the object product were low, and the process was found to be inadequate as an industrial process for making polymethylene polyphenyl polycarbamate.

It has also been recently disclosed by Japanese Laid-Open patent application No. 59264/1979 (U.S. Pat. No. 4,146,727) that upon reacting N-phenyl carbamate with formaldehyde by the above-described process, aminobenzylanilines are by-produced besides polymethylene polyphenyl polycarbamate, and when the reaction product containing the by-product is heated to 50°–170° C. using a protonic acid or a Lewis acid in anhydrous state, the aminobenzylanilines can be converted to polymethylene polyphenyl polycarbamate. By that method, however, first large quantities of by-products are formed because the condensation product is made by the heretofore known process, and, second, the condensation product must be dewatered and subjected to the rearrangement reaction under rigorous conditions. The two stage process requires complex procedures and is defective as an industrial process. Furthermore, although it is true that the aminobenzylanilines are decreased in the later stage rearrangement reaction, they are not necessarily effectively converted to the object product, but the greatest part is pyrolyzed to form high molecular polymers inadequate for obtaining polyisocyanate of high quality. Thus the intended product of satisfactory quality cannot be obtained.

SUMMARY OF THE INVENTION

An object of the present invention is to provide an improved process for making polymethylene polyphenyl polycarbamate with higher selectivity and yield. Still another object of the present invention is to provide an improved process for making polymethylene polyphenyl polycarbamate, which is economically advantageous and is suitable for industrial scale practice.

To wit, the invention provides process of reacting N-phenyl carbamate of the general formula (I) below:

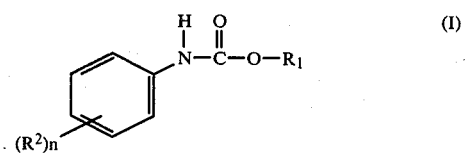

(in which $R_1$ represents a $C_1$–$C_6$ lower alkyl or cycloalkyl group, $R_2$ represents a hydrogen atom, halogen atom, $C_1$–$C_6$ lower alkyl or alkoxy group, and n is an integer of 1–4)

with formaldehyde or a formaldehyde-supplying substance in the presence of an acid catalyst, to make polymethylene polyphenyl polycarbamate of the general formula (II)

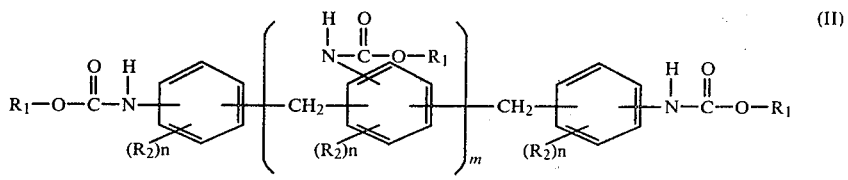

(in which $R_1$, $R_2$ and n have the same significations as those given as to the formula (I), and m is zero or an integer of 1–5), the characteristic feature residing in that the reaction is carried out in the concurrent presence of at least one compound or a mixture of at least two compounds selected from the group of compounds expressed by the general formulae (III), (IV), and (V) below.

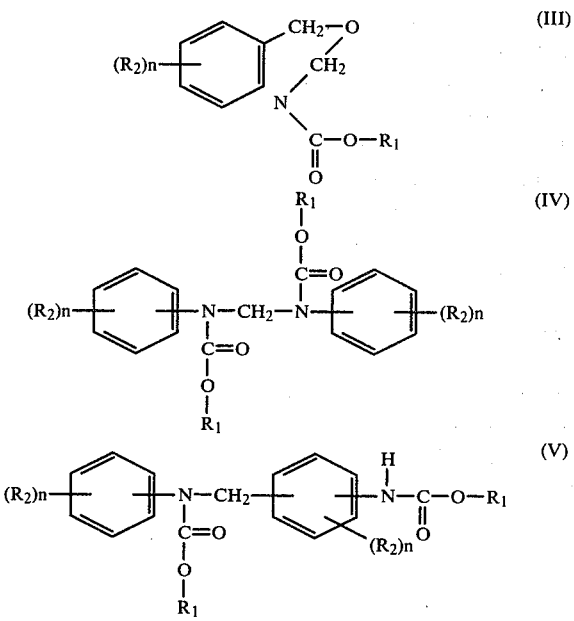

(in which $R_1$, $R_2$ and n have the same significations as in the general formula I).

The invention also provides a process as above, in which the compound or compounds selected from the group of compounds expressed by the general formula (III), (IV) and (V), which have been caused to be present in the reaction system, are recovered from the system after the reaction, and again caused to be concurrently present with the starting materials to effect the reaction for making polymethylene polyphenyl polycarbamate. The invention also provides a process as above, in which if an aqueous acid solution is used as the catalyst, the aqueous acid solution containing the organic impurities is separated and recovered after the reaction, and re-used without any interceding removal of the organic impurities but simply with the adjustment of its acid concentration.

In the heretofore known methods, for example, that disclosed in West German Pat. No. 1,042,891 and U.S. Pat. No. 2,946,768, wherein N-phenyl carbamate and formaldehyde are heated together with a diluted aqueous hydrochloric acid, the reaction progresses very slowly, and in the reaction mixture many organic impurities of unknown structures are present besides the object polymethylene polyphenyl polycarbamate. It is furthermore discovered that, those impurities are the objectionable compounds for the convertion of the reaction mixture to the corresponding polyisocyanate through pyrolysis. Our structural analysis of those organic impurities by such means as column chromatography, liquid chromatography, infrared absorption spectroscopy or nuclear magnetic resonance spectroscopy disclosed that, the impurities are composed chiefly of N-carboalkoxy (or cycloalkoxy)-2-oxa-4-aza-naphthalenes of the aforesaid general formula (III), bis[N-carboalkoxy (or cycloalkoxy)-anilino]methanes and N,N'-dicarboalkoxy (or cycloalkoxy)-aminobenzylanilines. We further studied the reactivities of those side-produced impurities, to find out that if the condensation reaction of N-phenyl carbamate with formaldehyde is carried out in the presence of the compounds of the general formulae (III), (IV) and (V), the side reactions can be inhibited, and the polymethylene polyphenyl polycarbamate of the general formula (II) can be produced at a higher selectivity and yield, compared with the case wherein such compounds are not concurrently present in the reaction system.

We have also discovered that, when the reaction of N-phenyl carbamate with formaldehyde is effected with an aqueous acid solution serving as the catalyst, after the reaction the aqueous acid solution can be easily separated and recovered from the organic layer containing the object product, and that the recovered aqueous solution contains unreacted N-phenyl carbamate, formaldehyde, the object product and the by-products of the formulae (II), (III), (IV) and (V), respectively. When the recovered aqueous solution is recycled into the subsequent fresh reaction system as it is, we found that the reaction progresses slowly. Hence, the solution cannot be repetitively used many times.

We searched for means to prevent the degradation in the catalytic activity of the recovered aqueous solution during the recycling uses, to find out that if its acid concentration is adjusted to a predetermined level before it re-use, the aqueous solution can assist the reaction at a constant rate, showing no-degradation in its activity although the organic impurities contained therein are not removed. That is, when an aqueous acid solution is used as the catalyst, the desirable acid concentration at the initiation of the reaction is at least 10% by weight, and the higher the acid concentration, the greater the reaction rate. This is a very surprising fact entirely unexpected, because in the well known condensation reaction, between formaldehyde and aromatic compounds, particularly aromatic amino compounds such as aniline, it has been proven that the lower is the acid concentration, the greater becomes the reaction rate [see, for example, Y. Ogata et al., *J. Amer. Chem. Soc.*, 37 1715 (1951)]. We also expected that the traces of organic compounds contained in the recovered aqueous acid solution would have generally detrimetnal effect on the solution's recycling use, but surprisingly, omission of their removal was found to have no adverse effect. Thus, in case N-phenyl carbamate is reacted with formaldehyde in the presence of an aqueous acid solution, said aqueous solution containing traces of organic impurities, which has been recovered after the reaction, can be re-used with its acid concentration adjusted to its initial level but without any purification treatment for removing the organic impurities. By such a practice the object polymethylene polyphenyl polycarbamate can be produced more economically, without decreasing the reaction rate.

DISCLOSURE OF THE PREFERRED EMBODIMENTS

N-phenyl carbamates to be used in the subject process are the compounds covered by the general formula (I). More specifically they are N-phenylcarbamates wherein, referring to said formula (I), for example $R_1$ is an alkyl group such as methyl, ethyl, n-propyl, iso-propyl, n-butyl, sec-butyl, iso-butyl, tert.-butyl, pentyl group derived from n-pentane and the isomers thereof, or hexyl group derived from n-hexane and the isomers thereof; or a cycloalkyl group from, for example, cyclopentane or cyclohexane; $R_2$ is a hydrogen atom, or a halogen atom such as chlorine, bromine and fluorine, or an alkyl group such as methyl, ethyl, n-propyl, iso-propyl, n-butyl, sec-butyl, iso-butyl, tert.-butyl, pentyl group derived from n-pentane and the isomers thereof, or a hexyl group derived from n-hexane and the isomers thereof; or an alkoxy group containing such an alkyl group as a constituent.

Such N-phenyl carbamates include N-phenyl-alkyl carbamate in which $R_1$ is one of the above-named alkyl groups and $R_2$ is hydrogen; N-halogenated phenyl-alkyl carbamate in which $R_1$ is an alkyl group as named above, and $R_2$ is the halogen atom as named already; N-alkyl-phenyl-alkyl carbamates in which $R_1$ and $R_2$ are the named alkyl groups; n-alkoxy-phenyl-alkyl carbamates in which $R_1$ is the aforesaid alkyl group and $R_2$ is the aforesaid alkoxy group; N-phenyl-cyclopentyl carbamates or N-phenyl cyclohexyl carbamates wherein $R_1$ is cyclopentyl or cyclohexyl group and $R_2$ is hydrogen; N-halogenated phenyl-cyclopentyl carbamates or N-halogenated phenyl-cyclohexyl carbamates wherein $R_1$ is cyclopentyl or cyclohexyl group and $R_2$ is the aforesaid halogen atom; N-alkylphenyl-cyclopentyl carbamates or N-alkylphenyl-cyclohexyl carbamates wherein $R_1$ is cyclopentyl or cyclohexyl group and $R_2$ is the aforesaid alkyl group; and N-alkoxyphenyl-cyclopentyl carbamates or N-alkoxyphenyl-cyclohexyl carbamates wherein $R_1$ is cyclopentyl or cyclohexyl group and $R_2$ is the aforesaid alkoxy group.

Of those, particularly preferred compounds are:
N-phenyl-methyl carbamate,
N-phenyl-ethyl carbamate,
N-phenyl-n-propyl carbamate,
N-phenyl-iso-propyl carbamate,
N-phenyl-n-butyl carbamate,
N-phenyl-sec-butyl carbamate,
N-phenyl-iso-butyl carbamate,
N-phenyl-tert-butyl carbamate,
N-phenyl-pentyl carbamate,
N-phenyl-hexyl carbamate,
N-o-chlorophenyl-methyl carbamate,
N-o-chlorophenyl-ethyl carbamate,
N-o-chlorophenyl-iso-propyl carbamate,
N-o-chlorophenyl-iso-butyl carbamate,
N-o-methyl-phenyl-methyl carbamate,
N-o-methyl-phenyl-ethyl carbamate,
N-phenyl-cyclohexyl carbamate,
N-o-chlorophenyl-cyclohexyl carbamate,
N-o-methyl-phenyl-cyclohexyl carbamate,
N-m-methoxy-phenyl methyl carbamate, and
N-phenyl-cyclopentyl carbamate.

The "formaldehyde-supplying substances" to be used in the subject process means para-formaldehyde, trioxane methylal and other formals.

The acids to be used in the subject process include such mineral acids as hydrochloric, sulfuric, phosphoric and boric acids; and such organic acids as formic, acetic, oxalic and toluenesulfonic acids. Also those super acids, such as hydrobromic, perchloric, chlorosulfonic and trifluoromethanesulfonic acids are effective.

Furthermore, ion-exchange resins having acidic groups such as carboxyl group or sulfonic acid group; and the acids normally referred to as Lewis acid, e.g. boron trifluoride, iron chloride, aluminum chloride, zinc chloride and titanium chloride, are also effective.

With the protonic acids such as the above-named mineral acids, organic acids and super acids, the amount of use is from 0.001 to 10 mols, preferably from 0.01 to 4 mols, per mol of the starting N-phenyl carbamate. When the acid is used as an aqueous solution, it is recommended to use it at the acid concentration of 10–95% by weight, preferably 20–80% by weight, to the water present in the reaction system, at the initiating time of the reaction. When it is below 10% by weight, the reaction rate becomes extremely low, making the process impracticable for industrial production. Whereas, when the acid concentration exceeds 95% by weight, objectionable side-reactions such as the hydrolysis of starting materials take place under high reaction temperatures.

For the recycling use of the recovered aqueous acid solution, it is recommended that the acid concentration should be adjusted to the above-specified range. Particularly when the acid concentration at the beginning of the reaction is adjusted to the equivalent level with that employed in the first batch reaction, the aqueous acid solution can be repetitively used, every time achieving an equal reaction rate. Thus the operation and control of the reaction can be much simplified.

It should be obvious that, if the acid concentration of the recovered aqueous acid solution is within the above-specified level, it can be used as it is. Normally, however, the acid concentration in the recovered solution differs from that before the reaction, due to the water formed of the reaction, loss into the reaction product layer, evaporation during the reaction, and the loss during the post treatment, and is apt to deviate from the specified range. Hence, it becomes necessary to adjust the acid concentration, for using the solution repetitively over many times.

All of the compounds which are expressed by the general formulae (III), (IV) and (V) and are caused to be concurrently present in the reaction system according to the present invention, have the structures derivable from the starting N-phenyl carbamates of the general formula (I). In said general formulae (III), (IV) and (V), $R_1$, $R_2$ and n have the same significations as those of the general formula (I), the specific examples thereof being the same to those mentioned as to said formula (I).

This is, the compounds expressed by the general formula (III) are N-carboalkoxy (or cycloalkoxy)-2-oxa-4-azanaphthalenes, and those of the formula (IV), bis(N-carboalkoxy (or cycloalkoxy)-anilino)methanes. Also the compounds covered by the general formula (V) are N,N'-dicarboalkoxy (or cycloalkoxy)aminobenzylanilines.

Those compounds can be produced by reacting the corresponding amino-compounds with halogenocarbonic acids alkyl esters. The compounds are also formed in the reaction of N-phenyl carbamates with formalin, together with polymethylene polyphenyl polycarbamates, and can be isolated from the reaction product by suitable means. Particularly bis(N-carboalkoxyanilino)methanes of the general formula (IV) can be obtained with a higher selectivity at a higher yield, by performing the reaction of N-phenyl carbamate with formalin using an acid catalyst, at the lowest temperature possible, while controlling the conversion of N-phenyl carbamate to 50% or below.

When the reaction of this invention is performed in the concurrent presence of any of those compounds in the reaction system together with the starting materials, sideproduction of the compounds (III) through (V) is inhibited during the reaction, and the yield of the object compound (II), i.e., polymethylene, polyphenyl polycarbamate, is improved. Furthermore, the use compound can be separately recovered from the reaction product, and repetitively re-used in the fresh reaction systems to achieve the above-mentioned effect.

The amounts of those compounds to be concurrently present in the reaction system vary depending on the purpose of their use, reaction conditions and means of the individual run, no generalized rules being applicable. Normally, however, they are used at a rate of 0.005–1 mol, preferably 0.01–0.5 mol, per mol of the starting N-phenyl carbamate, at the supplying time of the starting materials. In the fresh reaction system, normally N-carboalkoxy (or cycloalkoxy)-2-oxa-4-azanaphthalenes of the general formula (III) is formed in the amount of 0.005–0.2 mol per mol of the starting N-phenyl carbamate. Also bis(N-carboalkoxy (or cycloalkoxy)anilino)methanes of the general formula (IV) are formed at the ratio of 0.005–0.6 mol, and N,N'-dicarboalkoxy (or cycloalkoxy)-aminobenzylanilines, 0.005–0.3 mol. Hence, the compounds of the amounts within the above ranges are recovered from the first reaction system, to be recycled into the fresh reaction system.

Generally the subject process is practiced by heating the starting N-phenyl carbamate, the compounds of the general formulae (III), (IV) and/or (V), and formaldehyde or a formaldehyde-supplying substance, in the optional presence of a suitable solvent, together with an acid catalyst.

As the solvents which may be present in the reaction system, the following may be named for example: aliphatic hydrocarbons such as hexane and heptane; alicyclic hydrocarbons such as cyclopentane, cyclohexane and methyl cyclohexane; aromatic hydrocarbons such as benzene, toluene and xylene; and the alkyl-, halogen- and nitro-substituted compounds of the foregoing; halogenated hydrocarbons such as chloroform, methylenedichloride, carbon tetrachloride, dichloroethane, trichloroethane and tetrachloroethane; fatty acid alkyl esters such as ethyl acetate; and ethers such as diethyl ether, diisopropyl ether, dioxane and tetrahydrofuran. When such a solvent is used, its amount is normally 0.1–100, preferably 0.2–50 to the starting N-phenyl carbamate by the weight ratio.

The reaction temperature normally ranges from 10° to 150° C., preferably from 20° to 120° C. Exessively high temperatures invite objectionable side-reactions such as hydrolysis. The reaction time varies depending on the method and conditions of the reaction, but in the batchwise reaction system, it ranges from 1 minute to 10 hours, and in the continuous system, it is possible to reduce the actual contact time to less than one minute, by selecting adequate combination of the catalyst and reaction conditions.

The subject process can be practiced in a batchwise system wherein the starting N-phenyl carbamate, formaldehyde, the compound or compounds of the general formulae (III), (IV) and/or (V), an acid catalyst, and if necessary, a solvent, are charged into a reactor all at once. A continuous system may also be employed, in which the foregoing compounds are continuously supplied into the reactor, either all in one mixture or separately in suitable combinations, while the product is continuously withdrawn from the reaction system. Furthermore, so-called semi-continuous system may also be employed, wherein, for example, formaldehyde or a formaldehyde solution is dropwise added into N-phenylcarbamate, the compounds of the general formulae (III), (IV) and/or (V), an acid catalyst and optionally a solvent. Particularly the last-mentioned formaldehyde-dropping method frequently brings about favorable results, such as an improvement in the reaction rate and inhibition of side-reactions.

The subject process is normally practiced at normal pressure, but if necessary, either reduced or elevated pressures may also be employed.

When unreacted N-phenyl carbamate remains in the reaction product obtained of the subject process, it can be removed by such means as a reduced pressure distillation or an extraction with a N-phenylcarbamate-dissolving solvent. Whereas, the compounds of the general formulae (III), (IV) or (V) can be isolated and recovered, normally by the extraction with an adequate solvent, and re-used after the optional removal of said solvent. Depending on the type of the starting material, the object product can be precipitated in crystalline form upon cooling the reaction mixture containg the solvent, and thd unreacted N-phenyl carbamate and the compounds of the general formulae (III), (IV) and (V), which are to be recovered and re-used, remain in the liquid phase as dissolved in the solvent. Hence the filtrate remaining after removal of the precipitate by filtration is put to the recycling use.

When the reaction is practiced in the presence of an aqueous acid solution, normally N-phenyl carbamate is suspended in water or an aqueous acid solution, and into which formaldehyde (or a formaldehyde-supplying substance) and an aqueous acid solution are added, the mixture then being stirred at a predetermined temperature for a predetermined time. Thereafter the oil layer or a solid containing the object product is separated from the aqueous acid solution employing a conventional separating method, such as the liquid separation or filtration. Thus separated and recovered aqueous acid solution is preferably adjusted of its acid concentration to the equivalent level with the initial concentration, before it is re-used. That is, if its acid concentration is too high, it can be diluted with a suitable amount of water, and in an opposite case, the solution can be, for example, condensed.

The aqueous acid solution recovered according to the subject process is strongly acidic, and contains many organic substances. If it is discharged as it is, therefore, serious environmental pollution will be caused. If it is discharged as a harmless waste water through a suitable treatment, however, enormous expenses will be involved.

According to the subject process, the recovered acidic aqueous solution is recyclingly used. Hence, the starting materials can be economized compared with conventional processes, and furthermore the adoption of the closed system dispenses with the waste water discharge, perfectly preventing the environmental pollution. Thus the industrial merit of this process is indeed great.

Hereinafter the invention will be explained more specifically with reference to the working examples which, however, in no way limit the scope of this invention.

EXAMPLE 1

A 300 ml-flask equipped with a thermometer, a stirrer and a dropping funnel was charged with 18.2 g of N-phenylmethyl carbamate, 3.9 g of a compound of the general formula (III) in which $R_1$, $R_2$ and $n$ were respectively methyl, hydrogen and zero, i.e.,

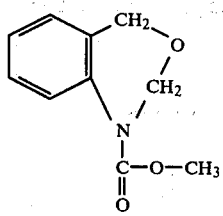

(N-carbomethoxy-2-oxa-4-azanaphthalene), 5.2 g of 35% aqueous formaldehyde solution, 35.4 g of 96% sulfuric acid and 32.3 g of water. The content was stirred for 4 hours at 80° C. After the reaction, 21.9 g of the organic layer was obtained. The analysis of the layer by a liquid chromatography, using naphthalene as the internal standard, disclosed that the layer was composed of unreacted N-phenylmethyl carbamate 5%, the polymethylene polyphenyl polycarbamate of the general formula (II) wherein $R_1$, $R_2$ n and m are respectively methyl, hydrogen, 0-5 and 1.78%, N-carbomethoxy-2-oxa-4-azanaphthalene 1%, the compound of the general formula (IV), i.e., bis(N-carbomethoxyanilino)methane, 2%, and the compound of the general formula (V), i.e., N,N'-dicarbomethoxyaminobenzylaniline, 4%, the percentages being by weight. This result signifies that the polymethylene polyphenyl polycarbamate yield to the reacted N-phenyl-methyl carbamate was 91%.

EXAMPLE 2

N-phenyl-methyl carbamate was reacted with formaldehyde in the identical manner with Example 1, except that 3.9 g of N-carbomethoxy-2-oxa-4-azanaphthalene was replaced with 3.1 g of bis(n-carbomethoxyanilino)methane. The organic layer obtained after the reaction weighed 22.3 g, which was composed of the unreacted N-phenylmethyl carbamate 5%, polymethylene polyphenyl polycarbamate 72%, N-carbomethoxy-2-oxa-4-azanaphthalene 1%, bis(N-carbomethoxyanilino)methane 2%, and N,N'-dicarbomethoxyaminobenzylaniline 4%, the percentages being by weight.

EXAMPLE 3

Example 1 was repeated except that 3.9 g of the N-carbamathoxy-2-oxa-4-azanaphthalene was replaced by 3.1 g of N,N'-dicarbomethoxyaminobenzylaniline. The results equivalent to those of Example 1 were obtained.

Control 1

Example 1 was repeated except that the use of N-carbomethoxy-2-oxa-4-azanaphthalene was omitted. After the reaction, 19 g of the organic layer was obtained, which was composed of the unreacted N-phenylmethyl carbamate 5%, polymethylene polyphenyl polycarbamate 77%, N-carbomethoxy-2-oxa-4-azanaphthalene 1%, bis(N-carbomethoxyanilino)methane 2%, and N,N'-dicarbomethoxyaminobenzylaniline 4%, the percentages being by weight. This result signifies that the polymethylene polyphenyl polycarbamate yield to the reacted N-phenyl-methyl carbamate was 81%.

EXAMPLES 4-6 AND CONTROL 2

In the preparation of a polymethylene polyphenyl polycarbamate by stirring a mixture of 20 g of N-phenyl-ethyl carbamate, 5.2 g of 35% aqueous formaldehyde solution and 67.7 g of 50% aqueous sulfuric acid, for 5 hours at 80° C., 4.1 g of N-carboethoxy-2-oxa-4-azanaphthalene was added to the starting reaction system in Example 4, 3.4 g of bis(N-carboethoxyanilino)methane, in Example 5, and 3.4 g of N,N'-dicarboethoxyaminobenzylaniline, in Example 6. In Control 2, none of such three types of compounds was added. The results were as shown in Table 1. In all of Examples 4-6, the polymethylene polyphenyl polycarbamate yields improved over that in Control 2.

TABLE 1

| | Additive | | Product | | | | | | Yield of (II) to |
|---|---|---|---|---|---|---|---|---|---|
| | (type) | (g) | (g) | (I) | (II) | (III) | (IV) | (V) | Starting (I) |
| Example 4 | (III) | 4.1 | 24.8 | 12 | 72 | 3 | 2 | 6 | 87 |
| Example 5 | (IV) | 3.4 | 24.6 | 10 | 74 | 2 | 3 | 7 | 89 |
| Example 6 | (V) | 3.4 | 23.7 | 11 | 73 | 2 | 3 | 8 | 84 |
| Control 2 | — | — | 20.8 | 11 | 72 | 2 | 3 | 7 | 73 |

Notes*
(I): N-phenyl-ethyl carbamate
(II): polymethylene polyphenyl polycarbamate
(III): N-carboethoxy-2-oxa-4-azanaphthalene
(IV): bis(N-carboethoxyanilino)methane
(IV): N,N'-dicarboethoxy-aminobenzylaniline

EXAMPLE 7

A 1-liter flask equipped with a thermometer, a stirrer and a dropping funnel was charged with 54.3 g of N-phenyl-methyl carbamate, 105.9 g of 98% sulfuric acid, 96.3 g of water and 75.2 g of dichloroethane. The content was heated on an oil bath to 50° C., under stirring, and into which 14.7 g of 37% aqueous formaldehyde solution was dropped through the dropping funnel. Thereafter the system was stirred at 80° C. for 4 hours. Cooling the system to room temperature, the resulting white solid precipitate was recovered by filtration, which weighed 34.0 g. Analyzing the solid by liquid chromatography using naphthalene as the internal standard, the product was identified to be a polymethylene polyphenyl polycarbamate composed mainly of bis(N-carbomethoxyaminophenyl)-methane. The purity of the polymethylene polyphenyl polycarbamate was 99%. After the separation of solid product, a two-phase solution composed of 196.5 g of the aqueous acid solution containing 46.3% of sulfuric acid and 0.02% of formaldehyde, and the dichloroethane solution containing 7.6 g of N-phenyl-methyl carbamate, 1.1 g of N-carbomethoxy-2-oxa-4-azanaphthalene, 1.6 g of bis(N-carbomethoxyanilino)methane and 2.7 g of N,N'-dicarbomethoxyaminobenzylaniline, was obtained. To the two-phase solution, freshly 46.7 g of N-phenyl-methyl carbamate was added, and reacted with 14.7 g of 37% aqueous formaldehyde by the above-described method. After the four hours' reaction at 80° C., the system was filtered to provide 45.3 g of a solid product which was identified to be a polymethylene polyphenyl polycarbamate of 98% purity.

The results of subsequent runs in which the recovered aqueous acid solution and the solvent were repetitively re-used in the similar manner to the above are collectively shown in Table 2.

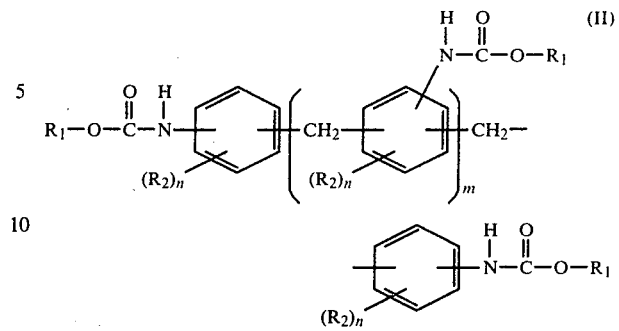

(in which $R_1$, $R_2$ and n have the same significations as in the case of general formula (I), and m is zero or an integer of 1–5), a process for making a polymethylene polyphenol polycarbamate which is characterized in that the above reaction is performed in the concurrent presence of a compound or a mixture of at least two compounds selected from those covered by the following three formulae (III), (IV) and (V).

TABLE 2

Charged amounts in every run: N-phenyl-methyl carbamate 46.7g (initially 54.3g)
37% aqueous formaldehyde solution 14.7g
Reaction temperature: 80° C.
Reaction time: 4 hours

| Number of re-used times | Acid concentration at the initiation of reaction* (wt %) | Acid/carbamate (mol ratio) | Product yield (g) | Product purity (%) | Recovered aqueous solution amount (g) | Recovered aqueous solution concentration (wt %) | N-phenyl-methyl carbamate content in the recovered dichloroethane solution (g) |
|---|---|---|---|---|---|---|---|
| initial run | 50 | 3 | 34.0 | 99 | 196.5 | 46.3 | 7.6 |
| 1 | " | " | 43.5 | 98 | 197.0 | 48.5 | 7.6 |
| 2 | " | " | 45.8 | 96 | 193.0 | 48.8 | 7.7 |
| 3 | " | " | 45.5 | 94 | 192.0 | 48.0 | 7.7 |

Note:
The acid concentration at the beginning of the reaction of each batch was adjusted to 50%, by analyzing the aqueous acid solution recovered after the preceding reaction and adding thereto necessary amount of 96% sulfuric acid.

What is claimed is:

1. In the process of reacting a N-phenyl carbamate of the general formula (I)

(in which $R_1$ is a $C_1$–$C_6$ lower alkyl or cycloalkyl group; $R_2$ is a hydrogen atom, halogen atom, a $C_1$–$C_6$ lower alkyl or alkoxy group, and n stands for an integer of 1–4) with formaldehyde or a formaldehyde-supplying substance, in the presence of an acid catalyst, to form a polymethylene polyphenyl polycarbamate of the general formula (II), 2. The process according to claim 1 wherein, in the general formulae (I), (II), (III), (IV) and (V), R₁ is a methyl group and R₂ is a hydrogen atom.

3. The process according to claim 1 wherein, in the general formulae (I), (II), (III), (IV) and (V), R₁ is an ethyl group and R₂ is a hydrogen atom.

4. The process according to claim 1 wherein, in the general formulae (I), (II), (III), (IV) and (V), both R₁ and R₂ are methyl groups.

5. The process according to claim 1 wherein, in the general formulae (I), (II), (III), (IV) and (V), both R₁ is an ethyl group and R₂, a methyl group.

6. The process according to claim 1, wherein the acid catalyst is selected from protonic acids such as mineral acids, organic acids and super acids.

7. The process according to claim 6, wherein the acid catalyst is sulfuric acid.

8. The process according to claim 1, wherein the acid catalyst is an aqueous acid solution having a concentration of 10–95% by weight to the water in the reaction system.

9. The process according to claim 1, wherein the reaction temperature ranges from 10° to 150° C.

10. The process according to claim 1, wherein the reaction is carried out in a solvent.

11. A process for making a polymethylene polyphenyl polycarbamate, which comprises reacting a N-phenyl carbamate of the general formula (I),

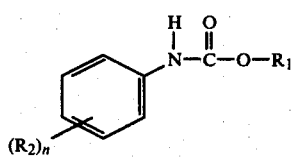

(in which R₁ is a C₁–C₆ lower alkyl or cycloalkyl group; R₂ is a hydrogen atom, halogen atom, a C₁–C₆ lower alkyl or alkoxy group, and n stands for an inter of 1–4) with formaldehyde or a formaldehyde-supplying substance, in the presence of an acid catalyst to form a polymethylene polyphenyl polycarbamate of the general formula (II)

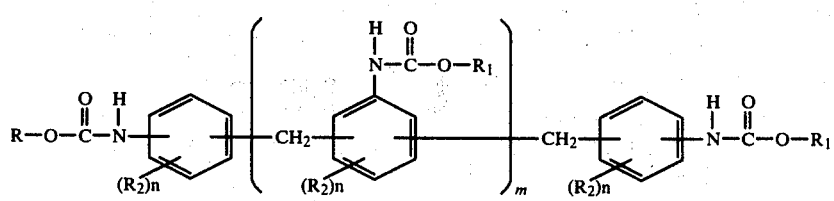

(in which R₁, R₂ and n have the same significations as those in the general formula (I), and m is zero or a positive integer of 1–5), the characteristic feature residing in that the reaction is effected in the concurrent presence of a compound or a mixture of more than one compound selected from the compounds covered by the general formulae (III), (IV) and (V) below:

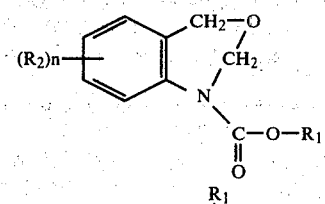

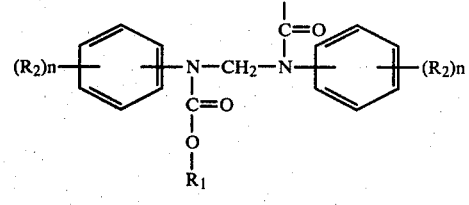

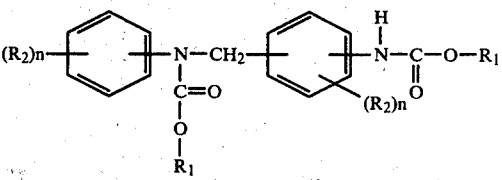

the process being furthermore characterized in that the compounds of the general formulae (III), (IV) and (V) are those recovered from the product which has been obtained by reacting a N-phenyl carbamate of the general formula (I) with formaldehyde or formaldehyde-supplying substance in the presence of an acid catalyst, or from the product obtained by carrying out the above reaction in the concurrent presence of a compound or a mixture of more than one compound selected from the compounds covered by the general formulae (III), (IV) and (V).

12. The process according to claim 11 wherein, in the general formulae (I), (II), (III), (IV) and (V), R₁ is a methyl group and R₂ is a hydrogen atom.

13. The process according to claim 11 wherein, in the general formulae (I), (II), (III), (IV) and (V), R₁ is an ethyl group and R₂ is a hydrogen atom.

14. The process according to claim 11 wherein, in the general formulae (I), (II), (III), (IV) and (V), both R₁ and R₂ are methyl groups.

15. The process according to claim 11 wherein, in the general formulae (I), (II), (III), (IV) and (V), R₁ an ethyl group and R₂, a methyl group.

16. The process according to claim 11, wherein the acid catalyst is selected from protonic acids such as mineral acids, organic acids and super acids.

17. The process according to claim 11, wherein the acid catalyst is sulfuric acid.

18. The process according to claim 11, wherein the acid catalyst is an aqueous acid solution having a concentration of 10–95% by weight to the water in the reaction system.

19. The process according to claim 18, wherein the aqueous acid solution is separated and recovered from the reaction system after the reaction, adjusted of the acid concentration and is recycled into the subsequent fresh reaction system.

20. The process according to claim 11 wherein, in the general formulae (I), (II), (III), (IV) and (V), $R_1$ is a methyl group or an ethyl group and $R_2$ is a hydrogen atom; the acid catalyst is a 10–95 weight percent aqueous sulfuric acid solution; the aqueous acid solution is separated and recovered from the reaction system after the reaction, adjusted of the acid concentration and recycled into the subsequent fresh reaction system; and the compound of the general formulae (III), (IV) or (V) which is contained in the reaction product is separated and recovered from the product and re-used in the subsequent reaction.

* * * * *